US005128150A

United States Patent [19]

Shanbrom

[11] Patent Number: 5,128,150
[45] Date of Patent: Jul. 7, 1992

[54] ALBUMIN ENHANCED ANTIVIRAL BLOOD PRODUCT TREATMENT AND PRODUCT PRODUCED

[76] Inventor: Edward Shanbrom, 2252 Liane La., Santa Ana, Calif. 92705

[21] Appl. No.: 425,466

[22] Filed: Oct. 23, 1989

Related U.S. Application Data

[63] Continuation-in-part of Ser. No. 321,522, Mar. 9, 1989, abandoned, and a continuation-in-part of Ser. No. 290,161, Dec. 28, 1988, Pat. No. 4,891,221, and a continuation-in-part of Ser. No. 276,113, Nov. 23, 1988, abandoned.

[51] Int. Cl.⁵ .............................................. A61K 35/18
[52] U.S. Cl. .................................... 424/533; 424/529; 424/530; 424/531; 424/532; 424/534; 435/2; 514/2; 514/6; 514/21

[58] Field of Search ................... 514/2, 6, 21; 435/2; 424/529, 530, 531, 532, 533, 534

[56] References Cited

PUBLICATIONS

Pompei et al—Chem. Abst. vol. 92 (1980), p. 122,494j.
Ichikawa et al—Chem. Abst. vol. 103 (1985), p. 115, 927v.
Nakano et al—Chem. Abst. vol. 97 (1982) p. 16, 493b.
Pompei—Chem. Abst. vol. 92 (1980) p. 104, 967m.

*Primary Examiner*—Sam Rosen
*Attorney, Agent, or Firm*—Grant L. Hubbard

[57] ABSTRACT

The treatment of blood product to inactivate or destroy infective viruses found in animal fluids and tissues, such as the cytomegalovirus, by mixing the blood product with an effective amount of glycyrrhizic triterpenoid compounds in combination with albumin is disclosed.

30 Claims, No Drawings

ALBUMIN ENHANCED ANTIVIRAL BLOOD PRODUCT TREATMENT AND PRODUCT PRODUCED

CROSS-REFERENCE TO RELATED APPLICATION

This is a continuation-in-part of my copending U.S. patent applications Ser. No. 07/321,522, filed Mar. 9, 1989, now abandoned, Ser. No. 07/290,161, filed Dec. 28, 1988, now U.S. Pat. No. 4,891,221, and Ser. No. 07/276,113, filed Nov. 23, 1988, now abandoned to which priority is claimed.

FIELD OF THE INVENTION

This invention relates to the treatment of mammalian biological organs, tissues, cells and fluids with one or more of a class of compounds referred to here as glycyrrhizic compounds, exemplary of which are glycyrrhizin, glycyrrhizinic acid or glycyrrhetinic acid glycoside, and analogous triterpenes, e.g. carbenoxolone and cicloxolone and their derivatives in combination with albumin, to inactivate virus found in animal fluids and tissues, such as cytomegalovirus, bovine diarrhea virus, human immunodeficiency virus and hepatitis viruses.

BACKGROUND OF THE INVENTION

This invention relates to the treatment of whole blood to inactivate or destroy infective viruses found in animal fluids and tissues, such as the cytomegalovirus which is responsible for or aggravates serious and sometimes fatal infections, in blood transfusion recipients.

Cytomegalovirus (CMV) is probably the most ubiquitous of the pathogenic viruses found in animal fluids and tissues. Virtually all of the people living in the developing countries become infected with CMV early in life, and CMV infects over half the population in the developed countries of the world. CMV may remain essentially inactive in the body following an initial infection and may flare in to an active infection any time, most frequently when the body's immune system is compromised to a greater or lesser degree by disease, radiation therapy, drug therapy, surgical trauma, etc. CMV is frequently associated with, and may be a causative or contributing factor in, life-threatening disease in individuals with suppressed immune systems, and can be a principal causative factor in pneumonia, neurological disorders, febrile illness, ocular disease and hepatitis. CMV infection is a serious limiting factor in the transplantation of organs, tissues and cells and the transfusion of blood and plasma from one individual to another. The kidney transplant patient runs a high risk of contracting serious, and not infrequently fatal, CMV infection from CMV introduced by the transplant organ. Recipients of whole blood, plasma, bone marrow, cornea, cardiac, and semen run a serious risk of CMV infectious disease, the risk being multiplied where the immune system of the recipient is suppressed to prevent rejection of the foreign organ or cells, or where immunosuppression is present from natural causes.

CMV is frequently associated with *Pneumoncystis carinii* and may cause or contribute to encephalitis and colitis and may be associated with Kaposi's sarcoma in AIDS patients. CMV is so ubiquitous in the blood and organs of donors who, frequently, exhibit no symptoms of infection, and its direct and contributory effects in infectious diseases is so pervasive and subtle that a CMV infection is to be presumed if another causative agent cannot be established.

There are no proven cures or generally effective drugs for the treatment of CMV infections. Certain drugs, e.g. ganciclovir, has been shown to have limited effectiveness in the treatment of certain CMV infections, e.g. CMV retinitis, but has little effect in the treatment of CMV pneumonia. Live attenuated CMV vaccine has been developed but may not protect against infection by natural CMV, and there is a real risk that the attenuated CMV may reactivate during pregnancy and infect the fetus.

While a method of preventing, or even reducing the likelihood of transmitting CMV via transfusion or transplant of organs, tissues, cells or fluids would be of enormous benefit to medical science, the present invention is not limited to treatments to inhibit CMV infection and is applicable to other classes of viruses found in animal fluids and tissues.

CMV is a member of the human herpesvirus (HV) group, which are responsible for much of mankind's discomfort and pain. The herpesviruses represent a very large, clearly defined group of viruses which are responsible for, or involved in, cold sores, shingles, a venereal disease, mononucleosis, eye infections, birth defects and probably several cancers. Three subfamilies are of particular importance. The alpha subfamily includes HV-1 (herpes virus simplex 1) which causes cold sores, fever blisters, eye and brain infections, HV-2 (herpes virus simplex 2) which cause genital ulceration, and HV-3 (HV varicella zoster) which causes chicken pox, shingles and brain infections. The beta subfamily includes HV-5, the principal member of which is CMV discussed above. The gamma subfamily includes HV-4 (Epstein-Barr) which cause infectious mononucleosis and is involved in Burkitt's lymphoma and nasopharyngeal carcinoma. Additional possibly pathogenic herpes viruses no doubt exist, one type of which, HV-6, of unknown pathogenicity has been identified. (Niederman, J. C. et al., The Lancet, Oct. 8, 1988, 817). There is evidence that the methods of this invention are effective in inhibiting the transmission of infections caused by many and perhaps all of the pathogenic herpes viruses found in animal fluids and tissues.

While blood bankers have instituted rigid criteria for exclusion of potential donors in high risk categories, this is not a satisfactory solution to the most significant threat to face the health care community in many decades. Institution of human immunodeficiency virus (HIV) testing has blood products safer, but the complete elimination of HIV contaminated blood and blood products has not been possible using present knowledge and technology. The ELISA test, for example, misses approximately 1 in 200 (0.5%) HIV infected donors, and there is no certain method for excluding donor carriers of hepatitis and other infectious viruses found in animal fluids and tissues. Increasing efforts are exerted to improve the safety of the blood supply such as retrovirus screening using surrogate markers, screening for HIV and other retroviruses with attention to population surveillance for newer agents, cleaner methods of extracting specific blood components by monoclonal antibody techniques and DNA methodologies, development of recombinant DNA products which by-pass the need for plasma derived clotting factors for administration to hemophiliacs. Careful screening of donors, followed by antibody testing, reduces the risk of AIDS and other virus-contaminated blood, but such methods are not foolproof. Such methods require testing supplies and trained technicians which are not available and are too expensive for use in such places as central Africa and other third-world countries where AIDS infects up to one-third of the population. A simpler and less costly method of handling blood is required in such areas of the world.

A photodynamic method has also been evaluated as a means of eradicating viral contaminants (Matthews, J. L. et al., *Transfusion*, 28,1 1988) but has not been proved to be generally effective and safe. While Factor VII products may be rendered non-infectious by heat or solvent-detergent methods, no methods are known to guarantee the safety of whole blood or cellular components or plasma. For the whole blood recipient, however, the only reasonably reliable safety procedures are programs allowing for self donation prior to elective surgery by the donor and the use of blood from designated donors, but such programs are incredibly difficult logistically. In spite of heroic efforts to meet the challenge of virus contaminated blood supply, an imperative need continues to exist for a method for treating whole blood for use in transfusion. It is apparent from the foregoing discussion that a method of killing or inactivating pathogenic viruses in organs, tissues, cell and fluids intended for transfusion or transplantation would be an enormous advance in medicine. It is to this major national and worldwide health care challenge that the present invention is directed.

Glycyrrhizic acid, 20B-carboxy-11-oxo-30-norolean-12-en-3B-yl-2-O-B-D-glucopyranuronsyl-$\alpha$-D-glucopyranosiduronic acid, commonly known as glycyrrhizin, glycyrrhizinic acid or glycyrrhetinic acid glycoside (also referred to as biosone, enoxolone, and glycyrrhetin) an extract from Glycyrrhiza, better known as licorice, an extract of the dried rhizome and roots of Glycyrrhiza glabra, is a triterpene and is exemplary of the triterpenes to which this invention relates. Analogous triterpenes to which this invention relates include carbenoxolone and cicloxolone. This invention thus relates to glycyrrhizic acid and analogues thereof, in the form of acids, salts, esters and other derivatives. Many such derivatives are known, such as, for example, glycyrrhetinyl stearate; monopotassium glycyrrhetin; potassium glycyrrhetinate; 11-deoxoglycyrrhetinic acid hydrogen maleate sodium salt; $\alpha$-D-glucopyranosiduronic acid monoarginine glycyrrhizinate; 18$\alpha$-Glycyrrhizic acid monosodium salt; 18-$\alpha$-Glycyrrhizic acid monopotassium salt; disodium 18-$\alpha$-glycyrrhizate; glycyrrhizinic acid mono(triethanolamine) salt; trisodium glycyrrhizinate; sodium glycyrrhizate; ammonium glycyrrhizinate; sodium carbenoxolone (biogastrone; glycyrrhetinic acid hydrogen succinate disodium salt); and acetylglycyrrhetic acid (glycyrrhetinyl acetate). Glycyrrhizin and the virucidal analogues and derivatives thereof are referred to for convenience herein as glycyrrhizic triterpenoids abbreviated GTPD. Presently the principal GTPD compounds of interest are glycyrrhizin (coded TPD-1 in some of my work), carbenoxolone (coded TPD-2 in some of my work) and cicloxolone.

Ring-substituted derivatives of GTPD compounds are contemplated and are included in this invention. Halogen ring substituents, such as, for example, fluoro- and chloro-substituents, sulfate and other active and/or inactivating substituents to the ring structure of GTPD compounds are specifically included in this invention, without excluding other ring-substituted derivatives of GTPD compounds.

In addition to its use as a flavoring agent, licorice has long been a common folk medicine for the treatment of sore throats. While not widely known, various extracts of and preparations derived from licorice, e.g. glycyrrhizin and its derivatives, principally the salts of glycyrrhizic acid, have also been used to a limited degree for many years as an orally administered medication for the treatment of peptic ulcers (Chandler, R. F., *Can. Pharm. J.*, V118, No. 9, 1985), and oral administration of glycyrrhizin contemporaneously with saponin antiinflamatory agents has been reported to inhibit saponin and saponigen hemolysis (Segal, R. et al., *Biochem. Pharmacol.* 26,7 1977).

GTPDs have been evaluated extensively in vitro, and have been administered orally, intramuscularly and intravenously. No significant toxicity from limited, short term administration of glycyrrhizin has been reported. Adverse reactions have been reported in certain instances of prolonged oral ingestion and a slight relapse after rapid discontinuation of intravenous administration of Stronger Neo-Minaphagen C (SNMC) solution, glycyrrhizin (0.2%), cysteine (0.1%) and glycine (2%) was attributed to the steroid ring in glycyrrhizin (Fujisawa K. et al., *Asian Med. J.* (Japan), 23,10 1980). Dosages of SNMC as high as 60 ml/day (~12 mg/dy of glycyrrhizin) have been reported (Iwamura K., Therapiewoche (W. Germany) 30,34 1980).

Inactivation of viruses, in vitro, under certain conditions, has been reported (see, e.g., Pompei R., *Exprientia* (Switzerland) 36/3 1980). Such anti-viral activity as GTPD compounds sometimes exhibit has been attributed to reverse transcriptase-inhibitory activity (Nakashima, H. et al., *Jpn. J. Cancer. Res.* 78,8 1987) and to enhancement of interferon-gamma production (Shinada, M. et al., *Proc. Soc. Exp. Biol.* 181,2 1986), but the exact mechanism of the anti-viral function has not been confirmed.

Dargan, D. J., and Subak-Sharpe, J. H., (J. Gen. Virol., 1985-1986) reported antiviral action of carbenoxolone and cicloxolone on herpes simplex virus. Their dose-response experiments showed cicloxolone sodium or carbenoxolone sodium interfered with the HSV replication cycle and reduced the infectious virus yield by 10,000- to 100,000-fold, cicloxolone being the more potent anti-herpes agent, but no consistent effect on HSV DNA synthesis was identified. Some inhibition of cellular DNA synthesis was observed, but this was relatively slight.

Csonka, G. W. and Tyrrell, D. A. (*Br. J. Vener. Dis.* 1984, 60 (3) p 178) undertook a double blind clinical study to compare the efficacy of carbenoxolone and cicloxolone creams with placebo in initial and recurrent herpes genitalis and reported significant differences in the time to disappearance of pain and the healing of lesions using cicloxolone, but carbenoxolone showed insignificant beneficial effect.

GTPDs have also been evaluated therapeutically as anti-viral agents in the chemotherapy of acquired immune deficiency syndrome (AIDS) (Ito, M., Yamamoto, N., *Yakaguaku Zasshi* (Japan) 188,2 1988), treatment of Epstein-Barr virus (EBV) infections (Van Benschoten, M. M., *Am. J. Acupunct*, 16,1 1988), and in the treatment of chronic hepatitis (Fujisawa, K. et al., *Asian Med. J.* (Japan), 23,10 1980).

The anti-viral activity of GTPDs varies so unpredictably as to preclude any generalized statements as to whether such compounds have general anti-viral effect or even as to whether such compounds will generally have anti-viral value as to any given virus. While GTPD drugs do, in some environments and under some conditions, exhibit some activity against some viruses, no anti-viral therapy based on GTPDs or in vitro anti-viral application of GTPDs has been generally accepted. The AIDS-causing viruses, HIV-I and HIV-II, are the first retroviruses identified as pathogenic in man. While HIV are more fragile than most infectious viruses and are susceptible to destruction by most virus-inactivating methods, such as heating, use of detergent compounds, etc., these methods also damage cells, e.g. the red blood cells, and, therefore, are not suitable for use in treating blood. In addition, any substance added to blood will, unless removed, remain in the blood, and must, therefore, be non-toxic when administered intravenously. Removal of added toxins from blood is, at best, complex and expensive and may not be feasible or possible without serious damage to blood components.

The major constituent of plasma is albumin whose primary role is that of osmotic regulation; it is responsible for 75-80% of the osmotic pressure of plasma. Albumin also serves important roles in the transport of small molecules such as drugs.

An important feature which segregates albumin from other colloids as well as crystalloids is its unique ability to bind reversibly with both anions and cations; hence, albumin can transport a number of substances including fatty acids, hormones, enzymes, dyes, trace metals, and drugs. Substances which are toxic in the unbound or free state are generally not toxic when bound to albumin. This binding property also enables albumin to regulate the extracellular concentration of numerous endogenous as well as exogenously administered substances.

Albumin in general has three types of binding sites (one for acidic, one for basic, and one for neutral compounds), and it plays a critical role in the binding and transport of lipid and lipid-soluble material. Albumin binds with and transports many administered drugs. Because of the phenomenon of mutual displacement of similar type substances, adverse drug interactions may occur. This phenomenon may have important ramifications during disease states such as sepsis, burn injury, and circulatory shock due to a number of etiologies, especially in conjunction with treatment with drugs which may be toxic at high concentrations.

Human serum albumin is believed to be a scavenger of oxygen-free radicals, an important phenomenon which also extends to scavenging of radicals required for lipid peroxidation.

Albumin is a potent scavenger of oxygen radicals. Concentrations of human serum albumin below those present in normal human plasma completely inhibit the inactivation of $\alpha_1$-antiproteinase ($\alpha_1$-proteinase inhibitor [$\alpha_1$-PI], $\alpha_1$-antitrypsin) by hypochlorous acid.

Preliminary work in the endotoxemic sheep adult respiratory distress syndrome (ARDS) model also demonstrated that pretreatment with human serum albumin markedly attenuates the 300% to 400% increases in pulmonary lymph flow, transvascular protein clearance, and transvascular protein flow which normally occurs during endotoxemia. UNIQUE FEATURES OF ALBUMIN: A BRIEF REVIEW, Thomas E. Emerson, Jr., Ph.D., *Critical Care Medicine*, Vol. 17, No. 7 (1989).

Treatment with human serum albumin to bind toxic products generated during inflammatory disease states has not received widespread attention. However, a few studies and the inherent ability of albumin to bind numerous toxic plasma substances support the concept.

Albumin is critical for the transport of numerous compounds, especially non-water soluble ones. It binds with iron and lipids and other potentially toxic substances, e.g., bilirubin. Thus albumin acts as a buffer to prevent increases in potentially cytotoxic endogenous lipid-soluble substances by binding with, and thus limiting, increases in plasma and interstitial fluid concentrations of these substances.

In addition to displacement of on albumin-bound drug by another, endogenous substances may also alter significantly the unbound or "free" plasma and interstitial fluid concentration of a drug. For example, as the concentration of bilirubin increases in certain disease states, a drug which occupies the same binding site as bilirubin will be displaced by the bilirubin, and the plasma concentration of the free drug will increase, possibly to toxic levels. Also, as the plasma concentration of albumin decreases, the plasma and interstitial fluid concentration of the unbound (free) drug will increase.

Plasma albumin concentration is usually decreased to varying degrees in disease states such as sepsis, burn injury, and circulatory shock. Resuscitation with large volumes of non-albumin colloid or crystalloid solutions will further decrease an already low albumin concentration and may consequently further limit the ability of albumin to modulate the free concentration and transport of toxic substances or drugs administered for therapeutic purposes.

Another feature of albumin is its inhibitory effect on pathologic platelet aggregation, which may be due to a greater affinity of arachidonic acid for albumin than for platelet-generated cyclooxygenase. It has also been demonstrated that albumin enhances the inhibition of factor Xa by antithrombin-III (AT-III).

In addition to the well-known role of albumin in generating colloid osmotic pressure, it also may protect the lung and other organs from edema by preserving microvascular integrity.

Very recent work support a role for albumin in the maintenance of normal microvascular permeability to protein.

It is known that albumin binds to glycyrrhizic triterpenoids. Carbenoxolone is a potent ulcer-healing drug which is extensively bound to plasma proteins and therefore has the potential for displacement interaction. Carbenoxolone has been shown to be bound to human serum albumin in vitro at a different class of binding site to many other drugs and does not potentiate the pharmacological activity of warfarin, tolbutamide, chlorpropamide or phenytoin in the rat. Thornton PC; Papouchado M; Reed PI *Scand J Gastroenterol Suppl* 1980, 65 p35-9.

The binding of glycyrrhizin to human serum and human serum albumin (HSA) was examined by an ultrafiltration technique. Specific and nonspecific bindings were observed in both human serum and HSA. The association constants (K) for the specific bindings were very similar: $1.31 \times 10^5 M^{-1}$ in human serum and $3.87 \times 10^5 M^{-1}$ in HSA. Glycyrrhizin binds to only the albumin fraction. It was concluded that the glycyrrhizin-binding sites in human serum exist mainly on albumin and glycyrrhizin binds to specific and nonspecific binding sites at lower and higher concentrations than approximately 2 mM, respectively. Ishida S; Sakiya Y; Ichikawa T; Kinoshita M; Awazu S, *Chem Pharm Bull* (Tokyo) 37 (1). 1989. 226–228.

Comparison by equilibrium dialysis of plasma protein binding sites for carbenoloxone in people under 40 yr of age and in people over 65 yr of age showed that the number of binding sites was reduced in the elderly and that this fall was associated with a reduction in plasma albumin levels. Hayes M J; Sprackling M; Langman M, Gut 18 (12) 1977 1054–1058.

Albumin was been used as an emulsion stabilizer oil-and-water emulsion injectable medical preparations, e.g. fluorbiprofen, Mizushima et al., U.S. Pat. No. 4,613,505, Sep. 23, 1966; as a binding molecule for tryptophan, Pollack, U.S. Pat. No. 4,650,789, Mar. 17, 1987; with chemical modification as complexing agents for cholesterol derivatives, Arakawa, U.S. Pat. No. 4,442,037, Apr. 10, 1984; as conjugates with enzyme linked to an antibody, Poznansky, U.S. Pat. No. 4,749,570, Jun. 17, 1988; and as chemically coupled conjugates of leukotrienes, Young, et al., U.S. Pat. No. 4,767,745, Aug. 30, 1988.

Human serum albumin is a remarkable protein which performs numerous tasks critical to maintenance of the milieu interieur. The best known functions of albumin involve regulation of transvascular fluid flux and hence, intra and extravascular fluid volumes and transport of lipid and lipid-soluble substances. However, it is also involved in a number of other vital functions, some of which have only recently been suggested and perhaps others which are as yet unrecognized. Among recognized unique features of albumin are: a) binding, and hence, inactivation of toxic products; b) regulation of the plasma and interstitial fluid concentrations of endogenous and exogenously administered substances and drugs; c) involvement in anticoagulation; d) maintenance of microvascular permeability to protein; and e) scavenging of free radicals and prevention of lipid peroxidation. This latter property may prove to be critically important, particularly in inflammatory disease states in which free radicals are thought to be a major culprit in direct damage due to tissue oxidation and indirect tissue damage due to inactivation of important antiproteinases such as $\alpha_1$-PI and AT-II. See UNIQUE FEATURES OF ALBUMIN: A BRIEF REVIEW, Thomas E. Emerson, Jr., Ph. D., *Critical Care Medicine*, Vol. 17, No. 7 (1989).

Procedures for large-scale, i.e. at least one unit of blood, fractionation of whole blood into its component cell types and plasma, and methods for the preparation of isolated plasma protein fractions from plasma are well known. The principles of enhanced sedimentation, e.g. centrifugation, and adhesion can be used to separate anticoagulated whole blood into platelet concentrate, leukocyte concentrate, packed red cells or leukocyte-poor packed red cells, and platelet-rich or platelet-poor plasma. Techniques based upon these principles are available for the selective isolation of platelets (plateletpheresis), leukocytes (leukapheresis), and plasma (plasmapheresis), and for the separation of different leukocyte cell types (granulocytes, lymphocytes, and monocytes).

Methods are known for the fractionation of plasma into the commonly used therapeutic plasma protein preparations: albumin; antihemophilic factor; fibrinogen; immune serum globulins (both normal and specific); plasma protein fraction; and prothrombin complex. The most commonly used fractionation procedures involve the techniques of cold ethanol or polyethylene glycol precipitation, heat denaturation, and ion-exchange chromatography.

Hazards of viral hepatitis or pyrogen contamination of plasma fractions do exist, and precautions must be taken to minimize these risks.

Two methods have been used to classify the plasma proteins. The first method is based upon solubility in salt solutions. On this basis there are three categoriesf (1) euglobulins, those proteins insoluble in water at their isoelectric point and precipitated by 33% saturated (1.3M) ammonium sulfate; (2) pseudoglubulins, those proteins soluble in water at their isoelectric point and precipitated at ammonium sulfate concentrations between 33% and 48% saturation (2M); and (3) albumins, those proteins soluble in water at their isoelectric point and requiring ammonium sulfate concentrations greater than 50% saturation (2.06M) for precipitation. The second classification method is based upon electrophoretic mobility. The Schlieren pattern obtained from free boundary electrophoresis of normal human plasma has 6 peaks. The pattern obtained with normal human serum has 5 peaks. Each peak represents a family of proteins having similar electrophoretic mobility. By precipitating all proteins insoluble in 50 % saturated ammonium sulfate, the fastest moving peak was identified as albumin. The peak present in plasma but absent in serum was identified as fibrinogen. The ramining peaks were identified as globulins and named ALPHA 1-, ALPHA 2-, BETA-, and GAMMA -globulins in order of decreasing mobility. Each of these classifications represents a heterogeneous mixture of proteins grouped on the basis of solubility or electrophoretic mobility.

The plasma proteins serve a wide variety of functions in the human organism. Their roles in the maintenance of blood volume and other physical characteristics of blood, such as viscosity, are extremely important because blood, in order to perform any of its numerous functions, must be a rapidly circulating medium. If the volume of plasma falls, the pumping action of the heart is strained and there is increased to flow owing to the increased concentration of the red cells to the plasma. The blood volume depends on the balance between the hydrostatic pressure of the blood in the capillaries, which tends to expel liquid from the blood into the tissues, and the osmotic pressure (owing to the plasma proteins), which tends to draw liquid back into the blood. The major contribution to the osmotic pressure of plasma is from albumin because of its concentration and properties.

Albumin comprises more than 50% of the plasma proteins by weight. It has a relatively low molecular weight and a high net negative charge at physiological pH. Albumin solutions have relatively low viscosity because of the spherical shape of the molecule.

The major impetus for the development of fractionation methods was the need to provide large amounts of a blood volume expander for the treatment of battlefield injuries during World War II. A product was desired that would provide the require oncotic action, not require refrigeration, and be free from the transmission of disease. Human albumin was found to be the most acceptable therapeutic fraction. A fractionation method was developed during the 1940s by a group headed by Cohn at the Harvard Medical School. The procedures were scaled up at the Harvard pilot plant and made available to commercial laboratries under contract to the U. S. Navy to provide blood derivatives for the Armed Forces. The methods developed during this period, with some modifications, are still the most popular methods for the preparation of albumin and ISG.

Cohn and co-worker described methods for the separation and purification of the protein and lipoprotein components of human plasma. In each of these methods there was an initial separation of the protein components of plasma into a small number of fractions in which the major components are separated, and then into a large number of subfractions into which these components are further concentrated and purified. The methods involved lowering the solubility of proteins by reducing the dielectric constant of the solution by the addition of ethanol. Thus separations could be carried out in the range of low ionic strengths at which the interactions of proteins with electrolytes differ from each other markedly. The protein to be separated must have a high solubility when most other components of the system have low solubilities, or the converse.

The plasma used in the development of these methods was obtained from blood collected into sodium citrate anticoagulant. Acetate and carbonate buffer systems were used to adjust pH and ionic strength. Precipitation was carried out at the lowest convenient ethanol concentration and temperature, and at the optimum pH and ionic strength for each separation.

Although the fractional precipitation methods described above were found to be adequate for the purpose of producing large amounts of therapeutic concentrates of plasma proteins, a new procedure took advantage of the increased stability of proteins in the solid state. All of the proteins are rapidly precipitated by a combination of the effects of ethanol and zinc ion. Separations from the solid state are made by fractional extraction. Specific metal-protein interactions favor the separation of undenatured proteins by reducing the extremes of pH and ethanol concentration. The lowest pH used is 5.5 and the highest ethanol concentration is 19%. This methods, in its entirety, has never been put into large-scale use. The use of 95% ethanol reduces the amount of ethanol required and reduces the volume of solutions to be processed.

For many therepeutic indications a preparation called plasma protein fraction (PPF) is used interchangeably with albumin. PPF is albumin in a slightly less pure are ALPHA- and BETA -globulins and salts. PPF can be produced by eliminating precipitation IV4 and precipitating fractions IV4 and V in a single step. If this is done, a filtration of supernatant phase IV1 is required. PPF is more economical to produce than albumin and can be recovered in higher yield. All ISG for therapeutic use is prepared from large pools of plasma from many donors os that the final product will contain a broad spectrum of antibodies.

Alternative methods for the production of albumin and ISG are also known. An economical method for the preparation of albumin involves heat denaturation of the nonalbumin components of plasma. In this method, plasma or serum is heated to 70° C. in the presence of caprylate ions, under which conditions the globulins and fibronogen become denatured. The caprylate serves to stabilize the albumin against thermal denaturation. By manipulation of pH, all the denatured proteins are precipitated and removed, leaving albumin in solution.

A modified method for the production of albumin by the heat denaturation of the nonalbumin components has also been developed. This method allows for the separation of the coagulation factors and ISG, if they are desired, whereas the isolation of albumin can beging at any step. The albumin produced is further concentrated by polyethylene glycol precipitation or ultrafiltration. Several methods have been used for the preparation of heat stable plasma fractions rish in albumin, to be used as plasma volume expanders.

Zinc complexes have also been used for fractionation, a fraction obtained by desalting plasma with ion-exchange resins and thus precipitating euglobulins, has been described and fractionation scheme using polyphosphate as a precipitat has also been used. None of these methods yield a fraction with a sufficiently high albumin content to meet regulations of the FDA for albumin or plasma protein fraction (PPF). Polyethylene glycol (PEG) has become a very popular protein precipitant. It acts by concentrating the protein component in the inter-PEG spaces by a displacement mechanism.

Plasma fractionation schemes usign precipitants other than ethanol or PEG for the isolation of albumin and ISG have been developed and used successfully, primarily in Europe. Ethyl ether has been used as a precipitant in England. Rivanol and ammonium sulfate have been used in Germany and, in Franc, placental blood is fractionated with the use of chloroform, trichloroaceti acid, and ethanol as precipitants, Recently, Pluronic polyols (BASF Wyandotte Corp) and solid-phase maleic anhydride polyelectrolytes have been used successfully on an experimental scale.

Adsorption chromatography has been used for the purification of ISG. A large-scale method for the production of albumin utilizing PEG, adsorption chromatography, and gel chromatography has recently been developed. Continuous preparative electrophoresis, polarization chromatography, isotachopheresis and isoelectric focusing are all promising techniques for the large-scale purification of plasma proteins.

The major hazard in producign fractions from large pools of plasma is the transmission of virus, the most serious, being hepatitis. This is a danger both for the recipient of the fractions and for the workers in fractionation plants. It has been shown that fractionation workers, particularly those engaged in the preparation of plasma pools, are at high risk of developing hepatitis B. The high risk products are fibronogen, AHF, and prothrombin complex. The low risk products are fibrinogen, AHF, and prothrombin complex. The low risk products are ISG, PPF, and albumin. The lack of infectivity of PPF and albumin is attributable to heating the final products at 60° C. for 10 hours.

It is now required in the United States that all donors of blood or plasma be tested for the presence of hepatitis B surface antigen by radioimmunoassay or reversed passive hemagglutination. This screening reduces but does not prevent the transmission of hepatitis B virus. A major problem is the transmission of non-B hepatitis, for which there is no screening test. Recent evidence indicates that non-A, non-B hepatitis also invokes a viral agent.

Another hazard of plasma fractionation is the partial denaturation of some fractions such as ISG, caused by the fractionation methods. These denaturated proteins may have toxic effects or may be immunogenic in the recipients. Among these undesirable side effects is the significant degree of loss of biological compotence and the loss or blockage of many binding sites on albumin are lost by the inherent denaturation resulting from this pasteurization or heating process. According to present technology, the disadvantages of denaturation are more than compensated for by the increased stability and potency of concentrated fractions, but there remains a great need for a fully bio-component albumin.

The safest source of albumin, in many instances, is the patient's own blood, and it is known to remove the blood, accomplish a partial fractionation of the blood, treat one fraction of the blood and return the treated fraction to the patient. Ishizaki et al., U.S. Pat. No. 4,839,055, Jun. 13, 1989, describe a method for treating a blood which involves separating the blood withdrawn frrm a patient's body, mixing the condensed blood and the low molecular weight protein with a substitute liquid and returning the combined liquid into the patient's body.

It was discovered that glycyrrhizin, glycyrrhetinic acid, carbenoxolone and cicloxolone and the analogues thereof (glycyrrhizic triterpenoids or GTPD compounds) not only inactive HIV in blood and are known to be well-tolerated intraveneously but, in some instances, also serve as effective anticoagulants and cell-stabilizers and donot interfere with standard blood analyses, see my U.S. patent application Ser. No. 07/290,161, filed Dec. 28, 1988, now United States Patent (to be added).

SUMMARY OF THE INVENTION

It has now been discovered that albumin bingind to GTPD (glycyrrhizin, glycyrrhetinic acid, carbenoxolone and cicyxolone and the analogues thereof) does not reduce, and generally to enhances, the viral inactivation power of GTPD, and eliminate at low concentrations or greatly reduce any tendency of GTPD to hemolyze red blood cells. These discoveries are of enormous import, e.g. meaning, inter alia that GTPD can be carried into the system via albumin withoug losing its viral inhibition power, can be used at much higher concentrations than would otherwise be possible, and can be used where hemolysis is unacceptable.

It has now been discovered that combinations of GTPD compounds with albumin (GTPD-Albumin) exhibit striking and most unexpected advantages in viral inactivation.

Viral inactivation, as used here, means rendering the virus non-infective, i.e. the virus does not induce disease in a patient. In most instances traditional methods of quantifying virus population growth and reduction, e.g. log kill (see Fraenkel-Conrat, H., Kimball, P. C., and Levy, J. A. VIROLOGY, Second Edition, Prentice Hall, Englewood Cliffs, N. J., 1988, and Jakoby, W. H. and Pastan, I. H. (Eds), CELL CULTURE, (Volume LVIII of "Methods of Enzymology", Acedemic Press, Inc., New York, Chapter 11) are good indicators of viral inactivation. However, viral inactivation is accomplished by GTPD-Albumin beyond the log kill measurement since any remaining virus are incapable of infecting a patient and are incapable of replicating.

At least one of the retroviridae is susceptible to the treatment of this invention, according to presently available data. The most notorious of the retroviridae, HIV-1, the only virus thus far identified as inducing AIDS in humans, is inactivated and/or killed using the methods and compositions of this invention. Other retroviridae are considered to be susceptible to the present invention, and treatment to prevent transmission of retrovirus-infected organs, tissues, cells and fluids is within the scope of this invention.

The treatment of such organs, tissues, cells and fluids to prevent the transmission of hepandnaviridae-related infections, e.g. hepatitis, is also within the scope of this invention, but data regarding the actual effect of treatments on hepatitis infectivity is so difficult to obtain that reliable data providing the efficacy of the present invention in hepatitis infection inhibition are extremely difficult to obtain.

The present invention comprises methods for inactivating viruses in whole blood by the use of extracts of the well-known flavoring agent licorice, referred to here as glycyrrhizic triterpenoids or GTPD compounds in combination with albumin, GTPD-Albumin.

This invention relates to methods for collecting and treating whole blood with GTPD compounds, e.g. glycyrrhizic acid, its analogues such as carbenoxolone and cicloxolone, analogues thereof and the salts, esters and other derivatives thereof in combination with albumin, GTPD-Albumin, as an viral inactivation enhancing agent, and to whole blood for transfusion containing such compounds which is free of CMV virus capable of infecting the recipient of such blood. Inactivation of other viruses found in animal fluids and tissues also results.

This invention is embodied in the process of collecting blood from a donor comprising withdrawing the blood from the donor and introducing the blood into a whole blood container which contains an effective amount of a GTPD compound consisting essentially of glycyrrhizin, glycyrrhetinic acid, carbenoxolone, cicloxolone and analogues and derivatives thereof, or mixtures thereof in combination with albumin, GTPD-Albumin, as an viral inactivation enhancing agent for inactivating HIV and other viruses found in animal fluids and tissues and preventing coagulation of the collected blood.

This invention is also embodied in commercial blood containers which comprise an amount of a GTPD compound which consists essentially of glycyrrhizin, glycyrrhetinic acid, carbenoxolone, cicloxolone, analogues and derivatives thereof, or mixtures thereof in combination with albumin, GTPD-Albumin, as an viral inactivation enhancing agent in an amount effective to inactivate HIV and/or other viruses found in animal fluids and tissues. The GTPD compound also serves as an anticoagulant.

DESCRIPTION OF THE PREFERRED EMBODIMENT

The preferred method of carrying out the invention comprises providing a transfusion blood container which comprises an amount of the GTPD compound, e.g. glycyrrhizin, glycyrrhetinic acid, carbenoxolone or cicloxolone in combination with albumin, GTPD-Albumin, sufficient to inactivate CMV and/or other viruses in blood collected therein from a donor such that the GTPD comprises from about 0.001 weight/percent (w/%) to about 10 w/%, generally in the range of about 0.05 to about 3 w/%, of the collected blood when the container is filled.

The collected blood is held at normal room temperatures, or preferably at about 37° C. ± about 8° C., or for a longer period of time near 0° C., generally from about one hour to as much as twenty four hours or more to assure viral inactivation. Longer holding periods are equivalent in all essential respects with no significantly improved results. The holding period may be, and preferably is, immediately after collection, but may be at any stage in handling or processing. A holding period of from one-fourth hour to one hour at 45° C. is normally sufficient to assure that CMV and other blood borne viruses are inactivated. An overnight holding period, 12 to 24 hours, is sufficient even at lower temperatures. Careful mixing is desirable and is preferably conducted immediately after the first mixing of blood and GTPD-albumin mixture.

Albumin from any source which is safe for intravenous use may be used to form GTPD-Albumin for use in this invention. Conventional caprylate stabilized, heat treated albumin may be used, for example. GTPD-Albumin is prepared simply by mixing GTPD into an albumin solution and allowing the solution to equilibrate a sufficient period of time, a few minutes being sufficient, to assure homogeneity and the formation of GTPD-Albumin. It is convenient to form a saturated solution of GTPD-Albumin, allow it to stand overnight and, if necessary, to filter the solution to assure that any excess GTPD or any precipitate is removed, and then to dilute the GTPD-Albumin solution as desired, or use it full-strength as an additive to blood products.

In appropriate instances, the patient's own albumin may be used. If, for example, it is known sufficiently in advance that a patient will be receiving whole blood or a blood product, and if the patient's health permits, an appropriate amount of the patient's blood may be taken and fractionated sufficient to provide a fraction which does not contain red blood cells, contains the albumin, preferably delipidated albumin, of the patient. GTPD is then mixed into the albumin-containing fraction and the GTPD-Albumin is allowed to form by letting the mixture stand for a few minutes to a few hours. Prolonged standing or storage, e.g. several days to a few weeks, is not detrimental. The GTPD-Albumin is then mixed with the blood and the resulting blood (or blood product) mixture is maintained at a suitable temperature long enough, as discussed above, to inactivate the virus which may be in the blood product. For example, GTPD-Albumin may be prepared the day preceding or a few hours before elective surgery using the patient's own albumin. The GTPD-albumin is mixed with the transfusion blood product about an hour before expected use thereof and the GTPD-Albumin-blood product mixture is maintained at about 37° C.± about 8° C. for an hour or more and the virus-inactivated blood product is used to transfuse the patient.

Particularly striking results are accomplished using albumin which has not been stabilized in the traditional way, e.g. with caprylate, and has not been heated. According to the prior art, such an albumin product would be regarded as unsafe because of the potential presence of pathogenic virus. If, however, the stabilization step and the heating step are replaced by the addition of GTPD to the albumin, the virus are inactivated and the albumin is biologically competent. GTPD-Albumin formed in this manner has higher biological activity than GTPD-Albumin prepared from conventional albumin. In a test using a VSV/BVD sensitive cell line performed when the cells were in log phase, the samples were inoculated with $10^6$ pfu of vesicular stomatitis virus (VSV), incubated overnight and serially diluted in MEM with 10% FBS (fetal bovine serum), and then inoculated with VSV. The 0.10% GTPD (carbenoxolone) alone and 0.10% GTPD (carbenoxolone) in 5% solutions of various albumins wetr introduced at dilutions of from $1:10^2$ to $1:10^9$. The cells were examined daily for five days for virus caused CPE. The following table summarizes the comparative results.

| LOG KILL OF VSV BY TPD | |
|---|---|
| Albumin Used | Log Kill Five Days |
| None | 4.6 |
| Baxter Buminate ® (USP Lot 2746M011AA) | 1.3 |
| Miles Human Albumin Fatty Acid Free (Lot 82-324) | 1.6 |
| Hyland IS 9988 Human Albumin | 2.0 |
| Non-Stabilized, solvent detergent albumin[1] | 5.6+ |

[1] Human serum albumin prepared by Cohn Fractionation. Solvent-Detergent precipitation and alcohol ultrafiltration, not heated and no stabilizer, e.g. caprylate or tryptophan added.

It should be noted that at extreme dilutions of GTPD, binding to albumin may actually reduce antiviral activity; however, higher concentrations of GTPD can be used and the viral inactivation is not decreased even with the least biologically competent albumin and enhancement is generally observed.

Non-stabilized, non-heated albumin is, however, vastly superior to "conventional", i.e. stabilized and pasteurized, albumin, presumably because of a greatly increased ability to form GTPD-Albumin as a result of greater biological competence. Even at extreme dilution, an approximately 6 log dill was found. At lower dilutions (higher concentrations of GTPD) the kill was apparently complete, probably 7 to 9 logs.

It has also been found that the deactivation of antiviral power of GTPD by lipoproteins and/or fatty acids is eliminated or greatly reduced by adding the GTPD as GTPD-Albumin.

The ability of albumin to (a) bind GTPD, (b) not reduce and generally to enhance the viral inactivation power of GTPD, and (c) eliminate at low concentrations or greatly reduce any tendency of GTPD to hemolyze red blood cells is of enormous import. These results mean that GTPD can be carried into the system via albumin without losing its viral inhibition power, can be used at much higher concentrations than would otherwise be possible, and can be used where hemolysis is unacceptable.

As reported in the prior art, it is known that GTPD will bind to albumin. The nature of the binding, which results in GTPD-Albumin, is not fully understood. GTPD bound to albumin would be expected to be less active chemically and biologically. Quite surprisingly, however, it was found that the viral inactivation characteristics of GTPD bound to albumin were not only not decreased buy were, in some instances at least, enhanced. Perhaps the most interesting discovery, however, was that the tendency of GTPD to lyse erythrocytes at high concentrations of GTPD in blood or packed red blood cells was greatly reduced. At lower concentrations, GTPD, alone, actually stabilized red blood cells but at higher concentrations, GTPD tended to lyse red blood cells. This made it necessary to work with GTPD concentrations in blood and blood products within a fairly narrow range. GTPD can, however, be added to blood as GTPD-Albumin at two to five times the concentration which would lyse cells if the GTPD had been added alone with no discernable lysing of RBC. This permits the use of higher concentrations of GTPD, with more certainty of virus inactivation and less risk of lysing during mixing. GTPD-Albumin prepared from non-stabilized, non-heated albumin has even less tendency to hemolysis than GTPD-Albumin prepared from conventional albumin. Virus-inactivation by GTPD-Albumin from non-stabilized, non-heated albumin was also higher than that of GTPD-Albumin from conventional albumin. For example, a 5-6 log (complete) kill of vesicular stomatitis virus (VSV) in packed red blood cells was accomplished by adding GTPD-Albumin solution to give a GTPD concentration of 0.5% carbenoxolone and 10% albumin after a wait period of one hour at 45° C. without significant hemolysis.

There is no criticality as to the ratio of GTPD and albumin. Generally, however, albumin will be present, on a weight percent basis, in ratio of from about 5:1 to 100:1, or more. For example, GTPD will generally be in the concentration range of about 0.05 to about 3 w/% in the blood product and albumin will be in the concentration range of from about 0.25 w/% to 15 wt/%. It is convenient to prepare a near saturate solution of albumin and add the maximum load of GTPD which the solution will carry as GTPD-Albumin and dilute the solution as desired.

In carrying out this method, conventional blood collection containers may be used. Such containers are typically made of sterile polymer film and contain an anticoagulant. The collection, handling and administration of the blood by transfusion is the same as is conventionally carried out, save only for the processes involving preparation of the blood to containing the GTPD compounds in mixture with albumin.

The GTPD-albumin compositions of this invention may be added to conventional anticoagulants, e.g. citrate dextrose, citrate phosphate dextrose, EDTA, heparin, etc. to enhance the anticoagulant effect of these, or to replace, in whole or in part, such anticoagulants.

There is no criticality respecting the addition of GTPD-albumin compositions at the time of collection, as, for example, introducing blood into bags containing GTPD-albumin compositions, though there are some advantages of convenience in this approach and this approach reduces the risk to blood handlers after collection. GTPD-albumin compositions may be added after collection any time in the chain of handling the blood. It may be desirable to assure a satisfactory inactivation of pathogenic virus in blood to add GTPD-albumin compositions at two or more stages, such as at the time of collection and 24 or 48 hours later, or at any later time. If the blood is to be used for immediate transfusion, however, one careful thorough intermixing of a higher concentration of GTPD-albumin compositions with a shorter delay between collection and transfusion than would normally occur in the routine handling of blood.

1-MRC-5 cells (Bartels) were grown in FCS and Eagle's minimal essential medium with 50 µg/ml of gentamicin, as the starting cell medium. 2-Cytomegalovirus [ATCC; $10^7$ tissue culture infectious dose (50)] was added to three samples each of (a) the media, (b) blood A and (c) blood B. Glycyrrhizin in DMSO was added to one of the (a), (b) and (c) samples to a final concentration of 2 wt/%. Controls containing only media added to the same volume and DMSO in media were prepared. Six-hundred fold dilutions were used to infect MRC-% monolayers grown in glass coverslips inside glass vials. The inoculum was centrifuged at 1.000×g for 1 hr at room temperature, and 1 ml of fresh media was added to each vial. The cultures were incubated at 37° C. and observed daily for cytopathic effect. Seven-days post-infection the monolayers were fixed with methanol and stained by indirect fluorescent method using a CMV monoclonal antibody (Syva). No cytopathic effect was observed in the samples in which glycyrrhizin was present, while 3-4+ cytopathic effect was observed in the other samples. The fluorescent antibody technique showed no evidence of residual virus in blood treated with GTPD. Blood mixed with DMSO, and blood in media, tended to clot. Blood mixed with the glycyrrhizic compound did not clot, but slight hemolysis may have occurred. pH adjustments using KOH or NaOH, etc., may be required.

Of the readily available GTPD compounds, carbenoxolone is preferred for its anti-viral effectiveness; however, glycyrrhizin and cicloxolone, in particular, and other GTPD compounds may be used with various advantages depending upon the particular compound.

When GTPDs are added to whole human blood containing substantial amounts of lipids and lipoproteins the GTPD's are, over a period of time, absorbed or adsorbed or otherwise removed from solution as active compounds. The GTPD compounds when added as GTPD-Albumin, however, remain in the blood as effective viral inactivators for a much longer period of time, as compared with GTPD added alone.

The GTPD compounds may be used to form GTPD-Albumin in their acid form; however, it is always necessary to check the pH after adding the GTPD compound and, if necessary, adjust the pH to about 7.0-8.0, e.g. with NaOH or KOH, before using the blood, as certain acid form GTPD compounds drop the pH of blood and plasma significantly to the pH 4-5 range.

The acid form of the GTPD compounds is only slightly soluble in water but is quite soluble in dimethyl sulfoxide. The salt, e.g. ammonium, sodium or potassium salts, of the GTPD compounds are, generally, soluble in water, the sodium and potassium salts being more soluble than the ammonium salts. It is, thus, convenient to purchase or prepare the GTPD compounds as sodium or potassium salts.

The effectiveness of GTPD compounds in killing or inactivating virus has been verified in fetal bovine serum (FBS) where additions glycyrrhetinic acid in concentrations of 0.05 to 0.7 percent followed by adjustment to pH 6.5 and 7.4, respectively for various trials, established a 100% kill of the relatively resistant vesicular stomatitis virus (VSV) was accomplished in all cases.

The invention is embodied in an article of commerce comprising packaged transfusion blood in a container of whole human blood containing one or more glycyrrhizic triterpenoid compounds in an amount of from 0.001 to 10 wt/%, preferably from about 0.05 to about 3 wt/%, in the form of GTPD-Albumin.

The invention is also embodied in a method of preparing whole human blood or blood products for transfusion, comprising mixing such blood with one or more glycyrrhizic triterpenoid compounds, as GTPD-Albumin, in a concentration of from 0.05 to 10.0 wt/%, preferably from about 0.5 to about 3 wt/%, based on blood, sufficient to substantially inactivate at least CMV.

As a method of treating a patient, the invention is a process comprising transfusing the patient with blood comprising one or more glycyrrhizic triterpenoid compounds, as GTPD-Albumin, in a concentration of from 0.05 to 10.0 wt/%, preferably from about 0.5 to about 3 wt/%, based on blood, sufficient to substantially inactivate at least CMV.

As a method of collecting blood the invention is embodied in a process comprising introducing said blood into a transfusion blood container containing glycyrrhizic triterpenoid, as GTPD-Albumin, compound sufficient to comprise from 0.05 to 10 wt/%, preferably from about 0.5 to about 3 wt/% of the contents when the container is full.

The invention is also embodied in blood products resulting from the treatment of blood with GTPD-albumin compositions. Such derivatives may include, for example, platelet and leukocyte concentrates, plasma, plasma derivatives such as, for example, cryoprecipitate, panels of red blood cells used in blood typing, and blood or blood fractions used for blood analysis such as, for example, the traditional blood samples now routinely collected in vacuum tubes. In such applications, the GTPD-albumin compositions may be present in or added to the vacuum tubes or at any later stage, though there are significant advantages in using vacuum tubes containing GTPD-albumin compositions. Donor blood may be processed to yield following single-donor components. Multiple donor pools of plasma harvested from whole blood can be processed to yield derivatives such as albumin, plasma protein fraction, Factor VIII concentrate, immune serum globulin preparation and concentrates of other blood factors. GTPD-albumin compositions may with great advantage be added along with glycerol or glycerol-water before freezing blood factors or derivatives to obtain a synergistic stabilizing effect, namely the stabilizing of GTPD by glycerol and the stabilizing of the blood factor or derivative, or whole blood in preparing cryoprecipitate, by both glycerol and the GTPD compound(s). GTPD-albumin compositions may be used in cell wash solutions to stabilize blood cells, platelets and the like, and to prevent or inhibit coagulation of the cells. It is advantageous, regardless of the mode or purpose in processing blood, to inactivate pathogenic virus at the earliest reasonable stage in the handling chain and/or at specific points in the handling chain. The present invention is well adapted to any blood processing regime.

In all embodiments, the invention exhibits a number of surprising results. The spotty results reported in efforts to determine if, and to what extent, GTPD compositions are indeed virucidal agents led the art to believe, as has been reported, that "the likelihood of developing a blood additive that would kill HIV and HBV and have no effect on laboratory examination of blood seems small." (Peter C. Fuchs, M.L.O., Oct. 13, 1988). In addition, notwithstanding the prior art in which anti-viral activity, to the extent it exists, of GTPD compounds is uncertain, unpredictable and, as yet, unexplained, and the widely accepted proposition that no blood additive could be found which would inactivate blood-borne viruses without adversely effecting the blood, e.g. lysing the red blood cells and/or interfering with blood analyses, the present invention embodies processes and blood compositions in which these desired but hitherto unattainable results are accomplished with enhanced certainty and reduced risk of damage to blood cells.

The GTPD-albumin compositions can be mixed with other active compounds with synergistic results in inactivation of virus. Such synergistic and potentially synergistic compounds include glycerol, the anti-viral drug AZT, which is known to act synergistically with the GTPD compounds, dextrans, butyl hydroxy toluene, fatty acids such as oleic acid, chelating agents such as EDTA, and compounds of transition and heavy metals.

In the case of blood, plasma or other fluid collection in a bag, vacuum tube, vial or other container, a highly desirable and preferred method and apparatus are utilized. The GTPD-Albumin is in or associated with the container.

INDUSTRIAL APPLICATION

This invention has direct application in the blood banking industry.

What is claimed:

1. A method of preparing a blood product suitable for human therapeutic transfusion comprising introducing into a transfusion human blood product one or more glycyrrhizic triterpenoid compounds in an amount of from 0.001 to 10 wt/% in combination with from about five to one hundred times that amount of albumin, effective to substantially inactivate susceptible viruses in said human therapeutic transfusion blood product.

2. The method of preparing a transfusion blood product as defined in claim 1 wherein from about 0.05 to about 3 wt/% glycyrrhizic triterpenoid compounds are added.

3. The method of preparing a transfusion blood product as defined in claim 2 wherein at least one glycyrrhizic triterpenoid compound is carbenoxolone.

4. The method of preparing a transfusion blood product of as defined in claim 2 wherein at least one glycyrrhizic triterpenoid compound is cicloxolone or glycyrrhizin.

5. A method for preparing human blood product for transfusion, comprising mixing such blood product with GTPD-Albumin, said GTPD-Albumin comprising one or more glycyrrhizic triterpenoid compounds in a concentration of from 0.05 to 10.0 wt/% based on blood product and from about five to about one hundred times that amount of albumin, and holding the resulting mixture for a period of at least about one hour, the concentration being sufficient to substantially inactivate susceptible viruses.

6. The method of claim 5 comprising mixing said GTPD-Albumin containing glycyrrhizic triterpenoid compounds in an amount sufficient to form a concentration of from about 0.05 to about 3 wt/% in the blood product.

7. The method of claim 6 wherein the holding time is at least about 12 hours.

8. The method of claim 5 further comprising adding an additional amount of said glycyrrhizic triterpenoid compounds into such blood product approximately at or after the end of the first holding period to renew the concentration thereof to from about 0.05 to about 3 wt/% and holding the resulting mixture for a second holding period.

9. The method of claim 5 further comprising adding an additional amount of GTPD-Albumin containing said glycyrrhizic triterpenoid compounds into such blood product approximately at or after the end of the first holding period to renew the concentration thereof to from about 0.05 to about 3 wt/% and holding the resulting mixture for a second holding period.

10. The method of claim 5 further comprising the step of maintaining the temperature of the blood product at about 37° C.±about 8° C. during said holding period.

11. The method of treating a human patient comprising transfusing the patient with human blood product comprising GTPD-Albumin which comprises one or more glycyrrhizic triterpenoid compounds in a concentration of from 0.001 to 10.0 wt/% based on blood product in combination with albumin, sufficient to substantially inactivate susceptible viruses.

12. The method of claim 11 wherein said blood product comprises glycyrrhizic triterpenoid compounds in a concentration of from about 0.05 to about 3 wt/%.

13. The method of claim 11 wherein said blood product is held before transfusion at a temperature of about 37° C.±about 8° C. sufficient to inactivate viruses in the blood product.

14. The method of collecting blood product comprising introducing said blood product into a transfusion blood product container containing GTPD-Albumin, which comprises glycyrrhizic triterpenoid compound in combination with albumin, in an amount to assure that the GTPD comprises from 0.001 to 10 wt/% of the contents when the container is full.

15. The method of collecting blood product of claim 14 wherein the amount of glycyrrhizic triterpenoid compound is sufficient to comprise from about 0.05 to about 3 wt/% of the contents when the container is full.

16. A method for preparing blood product for processing to recover blood constituents, fractions or components, comprising mixing such blood product with GTPD-Albumin which comprises one or more glycyrrhizic triterpenoid compounds in a concentration of from 0.05 to 10.0 wt/% based on blood product in combination with albumin, and holding the resulting mixture for a period of at least about one hour, the concentration being sufficient to substantially inactivate susceptible viruses found in animal fluids and tissues within said time and then recovering said blood constituents, fractions or components.

17. The method of claim 16 comprising mixing said GTPD-Albumin into such blood product to produce a concentration of from about 0.05 to about 3 wt/% of glycyrrhizic triterpenoid compounds in said blood product.

18. The method of claim 17 comprising maintaining the temperature of the blood product at about 37° C.±about 8° C. during said holding period.

19. The method of claim 16 further comprising adding an additional amount of said glycyrrhizic triterpenoid compounds into such blood product approximately at or after the end of the first holding period to renew the concentration thereof to from about 0.05 to about 3 wt/% and holding the resulting mixture for a second holding period.

20. The method of claim 16 further comprising adding an additional amount of GTPD-Albumin into such blood product approximately at or after the end of the first holding period to renew the concentration said glycyrrhizic triterpenoid compounds to from about 0.05 to about 3 wt/% and holding the resulting mixture for a second holding period of at least the same duration.

21. A transfusion blood container for the introduction of one or more blood products, comprising:
a) a transfusion blood container;
b) an amount of one or more glycyrrhizic triterpenoid compounds sufficient to comprise from 0.001 to 10.0 wt/% of the contents of the container when full of the blood product; and
c) albumin in an amount from about five to about one hundred times the amount of said glycyrrhizic triterpenoid compounds, said glycyrrhizic triterpenoid compounds being present in an amount sufficient to substantially inactivate viruses contained in the blood product introduced into said container.

22. The transfusion blood container of claim 21 wherein said blood product consists essentially of one or more of the following: whole blood, platelet concentrations, leukocyte concentrations, plasma, plasma derivatives, and whole blood fractions.

23. A transfusion blood container for the introduction of one or more blood products, comprising:
a) a transfusion blood container; and
b) an amount of one or more glycyrrhizic triterpenoid compounds sufficient to comprise from about 0.5 to about 3 wt/%, of the contents of the container when full of the blood product(s); and
c) albumin in an amount from about five to about one hundred times the amount of said glycyrrhizic triterpenoid compounds, said glycyrrhizic triterpenoid compounds being present in an amount sufficient to substantially inactivate viruses contained in the blood product introduced into said container.

24. The transfusion blood container of claim 23 wherein said blood product consists essentially of one or more of the following: whole blood, platelet concentrations, leukocyte concentrations, plasma, plasma derivatives, and whole blood fractions.

25. A transfusion blood container for the introduction of blood products, comprising:
a) a transfusion blood container; and
b) an amount of a glycyrrhizic triterpenoid compound sufficient to comprise from 0.05 to 10.0 wt/% of the contents when full;
c) albumin in an amount of from about five to about one hundred times the amount of glycyrrhizic triterpenoid compounds; said glycyrrhizic triterpenoid compounds being present in combination with albumin, whereby to inactivate viruses contained in the blood product introduced into said container.

26. The transfusion blood container of claim 25 wherein said blood products comprise whole blood, platelet concentrations, leukocyte concentrations, plasma, plasma derivatives, and whole blood fractions, and combinations thereof.

27. Red blood cell-containing human blood product containing from 0.001 to 10 percent by weight of glycyrrhizic triterpenoid and from 0.005 to 50 weight percent added, delipidated or stabilized albumin.

28. The product of the process of claim 1.

29. The product of the process of claim 5.

30. The product of the process of claim 8.

* * * * *